United States Patent [19]
Wallace et al.

[11] Patent Number: 4,576,181
[45] Date of Patent: Mar. 18, 1986

[54] DISPOSABLE PRESSURE TRANSDUCER APPARATUS FOR MEDICAL USE

[75] Inventors: William D. Wallace, Salt Lake City; Christopher A. Cutler, Bountiful, both of Utah

[73] Assignee: Utah Medical Products, Salt Lake City, Utah

[21] Appl. No.: 608,761

[22] Filed: May 9, 1984

[51] Int. Cl.$^4$ .............................................. A61B 5/02
[52] U.S. Cl. .................................. 128/675; 128/748; 73/708
[58] Field of Search ................................ 128/672–673, 128/675, 748; 73/708, 715, 720, 740

[56] References Cited

U.S. PATENT DOCUMENTS

| | | | |
|---|---|---|---|
| 3,868,679 | 2/1975 | Arneson | 128/673 |
| 4,112,272 | 9/1978 | Jonsson et al. | 128/675 X |
| 4,198,989 | 4/1980 | Hawke et al. | 128/675 |
| 4,465,075 | 8/1984 | Swartz | 128/748 X |

OTHER PUBLICATIONS

COBE Laboratories, Inc., "20 Years of Reusables is Long Enough . . . ".
American Pharmaseal, "Introducing the American Pharmaseal Disposable Pressure Transducer", (U.S.A., May 1983).
Gould, Inc., "Enter Gould's New World of Transducer Technology."
Sorenson Research Co., Inc., "Disposable Transducer: Transpac. The Ultimate in Accuracy and Convenience", (U.S.A., 1983).
Norton Health Care Products, "The New Norton Disposable Pressure Transducer is Available in a Full Line of Preconnected Standard Systems," (U.S.A., 1983).
Information Resources International, Inc., "Patient Monitoring Disposables," pp. 1-18, 20 (U.S.A., Sep. 1983).
L. Cromwell et al., "Biomedical Instrumentation and Measurements," pp. 135-150 (U.S.A., 1980).
Medex, "Monitoring Configuration."
COBE Laboratories, Inc., "COBE Disposable Transducer."

Primary Examiner—Lee S. Cohen
Assistant Examiner—Angela D. Sykes
Attorney, Agent, or Firm—Workman, Nydegger & Jensen

[57] ABSTRACT

A novel disposable pressure transducer apparatus for monitoring human blood pressure. The apparatus includes a semiconductor pressure transducer, a temperature compensation circuit, and light shielding structures mounted on a dielectric substrate. The substrate is secured within a housing adapted to follow the pressure pulses present in a fluid filled catheter to be communicated to the pressure transducer by way of a gel placed in a hole provided in the substrate.

25 Claims, 7 Drawing Figures

DISPOSABLE PRESSURE TRANSDUCER APPARATUS FOR MEDICAL USE

BACKGROUND

1. The Field of the Invention

This invention relates to pressure transducers for medical use and, more particularly, to a novel, disposable pressure transducer apparatus for use in the direct measurement and/or monitoring of human blood pressure.

2. The Prior Art

When diagnosing and treating various bodily ailments, medical personnel often find it desirable to measure and/or monitor a patient's blood pressure. For example, blood pressure measurement and monitoring are frequently employed with patients suffering from shock or cardiovascular ailments. Advantageously, by measuring and/or monitoring the blood pressure of these and other types of patients, medical personnel are better able to detect blood flow difficulties and other cardiovascular problems at an early stage. As a result, the use of blood pressure measurement and monitoring may increase the likelihood that a patient can be successfully treated and/or provided with needed emergency assistance.

A variety of methods are currently used for measuring and/or monitoring blood pressure. For example, medical personnel frequently use various indirect blood pressure measurement techniques, such as measuring a patient's blood pressure by using a pressure cuff and a stethoscope. In addition, blood pressure measurements are often made using a number of direct measurement and monitoring techniques. Notably, when diagnosing and/or treating critically ill patients, such direct techniques are greatly preferred over any of the indirect techniques.

This preference for direct blood pressure measurement and monitoring in certain cases is due to several factors. First, the use of direct blood pressure measurement and monitoring greatly increases the accuracy of the blood pressure reading. Typical indirect techniques may, for example, yield errors as high as ten percent, whereas direct blood pressure measurement and monitoring techniques are generally accurate to within about one percent. In addition, direct monitoring techniques facilitate the continuous monitoring of a patient's blood pressure on a beat-to-beat basis. Direct blood pressure monitoring also enables the rapid detection of a change in cardiovascular activity, and this may be of significant importance in emergency situations. Further, direct blood pressure monitoring techniques can be readily used to measure and monitor a patient's blood pressure at a specific internal location, such as within the chambers of the heart. Because of these and other advantages, therefore, direct blood pressure measurement and monitoring has become part of the routine treatment for critically ill patients.

One of the most widely used techniques for direct blood pressure measurement and monitoring is called catheterization. In using this technique, a needle is first inserted into a peripheral blood vessel. For example, if it is desired to monitor arterial blood pressure, the needle may be inserted into the radial artery. If, on the other hand, venous blood pressure is to be monitored, the needle may be inserted into the antecubital, radial, jugular, or subclavian veins.

Once the needle is properly inserted, a special catheter is threaded through the needle and into the blood vessel. Importantly, this catheter is filled with some type of solution, such as, for example, a sterile saline solution. In addition, the catheter may be formed so as to facilitate the further threading of the catheter along the blood vessel. Thus, the catheter may be threaded through the needle and along the blood vessel until the tip of the catheter, which is located inside the blood vessel, is positioned at the particular point within the body at which it is desired to make the blood pressure measurement. Then, with the catheter thus in place, the needle may be withdrawn.

After the indwelling catheter is positioned within a patient as described above, the other end of the catheter is connected to pressure transducer. The catheter is generally also connected to a suitable continuous flush device or heparin drip to help prevent clotting around the tip of the catheter. The present transducer is then connected to some type of monitor device near the patient's bedside. Typical monitor devices include cathode ray tube display devices, digital display and/or recording devices, printers and plotters.

With the measurement equipment having been prepared for use in the above-described manner, any air bubbles within the catheter are next removed such that a continuous fluid column is provided from the pressure transducer to the tip of the catheter which is located within the patient's blood vessel. Then, as the patient's heart thereafter pumps blood, periodic pressure pulses are transmitted through the patient's blood vessels and along the fluid column in the catheter to the pressure transducer. The pressure transducer generates electrical signals representing the pressure pulses, and such signals are then amplified and displayed by the monitor device. Usually, the monitor device is used to display the patient's blood pressure as a function of time, this type of display being commonly referred to as the blood pressure waveform. A patient's blood pressure waveform can then be used by medical personnel to appropriately diagnose and treat the patient.

It will be readily appreciated that one of the most important components of the above-described blood pressure monitoring system is the pressure transducer. Significantly, the accuracy and reliability of the pressure transducer set an upper limit to the quality of the blood pressure data which can be obtained. Therefore, those skilled in the art of blood pressure monitoring have attempted to develop pressure transducers which have a high degree of reliability, sensitivity, and accuracy.

A typical pressure transducer for use in blood pressure monitoring systems comprises a thin diaphragm which is capable of being deflected by the pressure pulses which travel through the above-described fluid column in the catheter. Some type of mechanism is also provided for measuring the deflection of the diaphragm; and such a measuring mechanism usually comprises suitable electronic circuitry which is configured so as to generate an electrical signal representing the pressure exerted on the diaphragm.

While a variety of electronic mechanisms have been used to measure the deflection of a diaphragm in pressure transducers, perhaps the most common measuring mechanism which is currently in use comprises a resistive strain gauge, such a mechanism being quite similar to strain gauges that are commonly used in industrial applications. Basically, a resistive strain gauge comprises a thin resistive wire which is connected to the pressure diaphragm such that the wire is stretched whenever the diaphragm is deflected. In accordance with well-known principles, such a stretching of the wire causes the electrical resistance of the wire to increase. Assuming, therefore, that a constant voltage is being applied across the wire, such an increase in the wire's resistance will result in a corresponding decrease in the electrical current through the wire in accordance with Ohm's law. Thus, by continuously measuring the current through the wire, it is possible to obtain an electrical signal which represents the amount by which the diaphragm is being deflected and which, therefore, also represents the pressure being exerted on the diaphragm.

In order to increase the sensitivity and accuracy of the pressure measurement, it is common to connect four such resistive wires to a single pressure diaphragm. Typically, the wires are also connected together in a conventional Wheatstone bridge configuration. Moreover, two of the wires are connected to the diaphragm so as to be stretched when the diaphragm is deflected, while the other two wires are compressed as the diaphragm is deflected. Significantly, using this type of diaphragm/circuitry configuration, it is possible to obtain quite accurate measurements of even small pressure pulses acting on the pressure diaphragm.

Unfortunately, the above-described pressure transducers have typically been quite expensive to manufacture. Consequently, these transducers have generally been provided in the form of a reusable instrument which can be connected to a fluid-filled catheter by means of a disposable dome. Although such reusable pressure transducers can produce acceptable results, the use of such transducers has a number of significant disadvantages. First, since the transducer is to be used by a number of patients, it must be sterilized after each use; and this sterilization procedure can be both time consuming and expensive. Further, the repeated use and the uncertain life of the pressure transducer have made it difficult to accurately charge patients for the use of the transducer device. In addition, the transducer must undergo periodic maintenance in order to assure its proper functioning and operation. All of these factors have made the use of reusable pressure transducers somewhat burdensome and inconvenient.

With the growth of the semiconductor industry and the recent development of semiconductor pressure transducers, many of the above-mentioned problems of reusable transducers have been overcome. Using current semiconductor technology, it is now possible to provide the several required resistive elements on the surface of a single, bonded silicon chip. For example, these resistive elements may be implanted on a silicon chip used conventional ion implanting techniques. In addition, a portion of the chip may be etched away (such as, for example, by means of suitable chemicals), so as to form a thin pressure diaphragm. Thus, a single silicon chip can be formed to comprise both the pressure diaphragm and the measuring circuitry of a pressure transducer. Significantly, since such silicon chips are readily adapted to being mass produced, the total cost of pressure transducers can be reduced substantially. As a result of these developments, therefore, several manufacturers have recently placed disposable pressure transducers on the market.

Despite the advantages of using semiconductor chips in pressure transducers, however, the use of semiconductor transducers raises a number of additional problems which must be addressed. First, the output of semiconductor pressure transducers is typically temperature-dependent. Also, semiconductors (particularly silicon semiconductors), are quite sensitive to light, such that exposure of semiconductor pressure transducers to light can produce transient variations in the pressure readings. Additionally, as with other prior art pressure transducers, the pressure diaphragm and circuitry must be mounted such that thermal expansion and contraction of the diaphragm and circuitry will not subject the sensitive measuring circuitry to mechanical stress. Further, care must be taken to insure that the pressure transducer device is electrically isolated from the patient so that an electric shock will not be transmitted through the fluid column in the catheter and back to the patient. Some efforts have been made to solve each of these problems in the prior art semiconductor transducer devices, and these efforts are briefly discussed below.

In order to compensate for the temperature dependence of semiconductor pressure transducers, the prior art devices have typically included some type of temperature compensation circuitry. Such circuitry may comprise resistors, thermistors, or other electrical components which are designed to compensate for fluctuations in the transducer output which are caused by variations in temperature. In the various prior art devices, such temperature compensation circuitry may be located in a number of positions relative to the pressure diaphragm. For example, one prior art device provides the temperature compensation circuitry as part of a connector in a cable which is used to connect the transducer device to an external monitor.

The prior art devices have also attempted to compensate for the light sensitivity of semiconductors in a number of ways. For example, some prior art devices include a coating on the semiconductor transducer which is intended to shield the transducer from exposure to light. The prior art devices may additionally comprise some type of tinted plastic housing which surrounds the transducer. Such a tinted housing is also intended to shield the semiconductor transducer from light.

In addition, in order to minimize the difficulty caused by thermal expansion and contraction of the semiconductor transducer, prior art devices have typically mounted the transducer on a pyrex pedestal. Notably, pyrex has approximately the same coefficient of thermal expansion as silicon. Thus, the pyrex pedestal will expand and contract with variations in temperature in substantially the same manner as in silicon chip, thereby minimizing mechanical stress which may be caused by such thermal expansion and contraction.

Finally, electrical isolation of the prior art devices from a patient has typically been accomplished by various insulators. Such insulators may, for example, comprise part of a housing within which the electronic circuitry is contained.

While the prior art disposable pressure transducers represent an important improvement over the earlier reusable transducers, a number of significant difficulties remain. First, the the prior art disposable pressure transducers are not entirely effective in shielding the semiconductor transducer from exposure to light. As a result, the prior art devices sometimes produce incorrect transient pressure readings which may interfere with the subsequent analysis and use of the pressure data. In addition, a movement of the prior art devices will occasionally subject the sensitive pressure measuring circuitry to mechanical stress, thereby also producing transient fluctuations in the pressure readings. Because of these conditions, therefore, the prior art disposable pressure transducer devices will sometimes not produce data having the desired degree of accuracy.

Additionally, the electrical insulators in the prior art transducer devices have occasionally failed. When this happens, an electrical shock may be transmitted from the transducer device to the patient along the fluid-filled catheter. This, of course, represents a significant safety risk to the patient, particularly if the patient is already suffering from some serious illness or injury.

Further, the prior art disposable pressure transducers are typically quite complex, and they remain, therefore, relatively expensive to manufacture. For example, a number of separate, delicate assembly steps are often required in order to arrange the various components of the transducer devices into a single unit. Such assembly steps may, for example, include mounting a semiconductor transducer on a pyrex pedestal and thereafter securing the pedestal within a housing. Of course, the expense of manufacturing the prior art transducer devices increases the ultimate cost of the devices; and such increased cost makes it less desirable to dispose of the devices after only a single use.

BRIEF SUMMARY AND OBJECTS OF THE INVENTION

In light of the foregoing, it is a primary object of the present invention to provide a disposable pressure transducer apparatus which is accurate, safe and economical.

It is, therefore, an object of the present invention to provide a disposable pressure transducer apparatus wherein the semiconductor transducer of the apparatus is effectively shielded from exposure to light.

It is also an object of the present invention to provide a disposable pressure transducer apparatus wherein mechanical stress of the pressure measuring circuitry is minimized both during movement of the apparatus and during thermal expansion and contraction of the semiconductor transducer.

Further, it is an object of the present invention to provide a disposable pressure transducer apparatus wherein the electrical circuitry of the apparatus is effectively isolated from the patient, thereby minimizing the likelihood that the patient will receive an electrical shock from the apparatus.

It is a still further object of the present invention to provide a disposable pressure transducer apparatus which has a minimum number of component parts such that the transducer apparatus is easy to manufacture and assemble.

Consistent with these objects, the present invention is directed to a novel disposable pressure transducer apparatus for monitoring human blood pressure. The apparatus comprises a two-sided dielectric substrate sheet which has a hole therethrough. A semiconductor pressure transducer is mounted directly to one side of the dielectric substrate such that the portion of the transducer which forms the piezoresistive pressure diaphragm is positioned over the hole in the substrate. The pressure transducer is mounted to the substrate such that it is free to thermally expand and contract without being subjected to mechanical stress.

The pressure transducer is also covered by an opaque cap which prevents light from contacting the transducer. In addition, at least one side of the dielectric substrate may be coated with an opaque substance to further shield the semiconductor transducer from light. A temperature compensation circuit also is provided on the substrate by some suitable means, such as, for example, by silk-screening; and the substrate further has solder pads secured thereto for electrically connecting the circuit on the substrate to a monitor device. Significantly, the pressure transducer, the opaque cap, the temperature compensation circuit, and the solder pads are all positioned on the same side of the dielectric substrate sheet, thereby greatly facilitating manufacture and assembly of the apparatus.

The substrate, together with the above-mentioned components, is secured within a housing. The housing is provided with a fluid coupling passageway for connecting the housing to a catheter, and a second passageway extends from the fluid coupling passageway so as to communicate through the hole in the substrate with the pressure transducer. Both the second passageway through the housing and the hole in the substrate are filled with a silicone gel such that pressure pulses may be transmitted through the silicone gel to the pressure transducer. In addition, the silicone gel extends into the space between the housing and the dielectric substrate so as to form a fluid-tight seal, thereby providing electrical isolation of the transducer apparatus from the patient. A portion of the silicone gel may also be opaque so as to help further shield the semiconductor transducer from exposure to light.

These and other objects and features of the present invention will become more fully apparent from the following description and appended claims, taken in conjunction with the accompanying drawings.

DETAILED DESCRIPTION OF THE PREFERRED EMBODIMENT

It will be readily appreciated that the components of the present invention, as generally described and illustrated in the figures herein, could be arranged and designed in a wide variety of different configurations. Thus, the following more detailed description of the embodiment of the apparatus of the present invention, as represented in FIGS. 1 through 5, is not intended to limit the scope of the invention, as claimed, but it is merely representative of one presently preferred embodiment of the invention.

Figure 1:
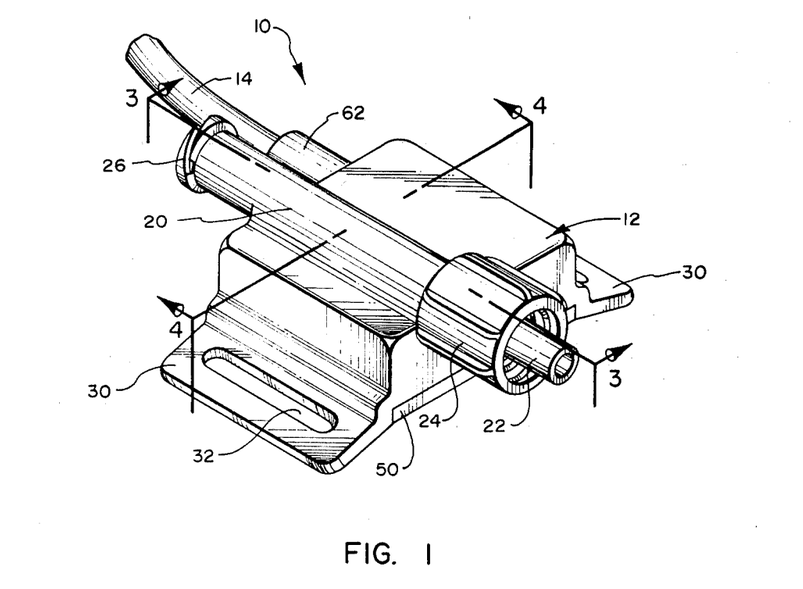
FIG. 1 is a perspective view illustrating one presently preferred embodiment of the disposable pressure transducer apparatus of the present invention.

Referring first to FIG. 1, the various pressure sensing components of transducer apparatus 10, which will be described in more detail below, are contained within a housing 12. As illustrated, housing 12 is provided with a fluid coupling tube 20 which may be connected to a catheter (not shown). In addition, a cable 14 extends from housing 12 and serves to carry electrical signals which represent the pressure measurements made by transducer apparatus 10 to a monitor (not shown).

In use, a catheter which is inserted into a blood vessel of a patient is connected to coupling tube 20 of transducer apparatus 10. Pressure pulses from such patient's blood stream are then transmitted through the fluid column in the catheter through the passageway of coupling tube 20. The pressure detection components within housing 12 detect and measure the pressure pulses and generate electrical signals representing such pulses. The generated electrical signals are then transmitted along cable 14 to a monitor (not shown) such that the pressure data may be appropriately displayed and/or recorded.

Figure 2:
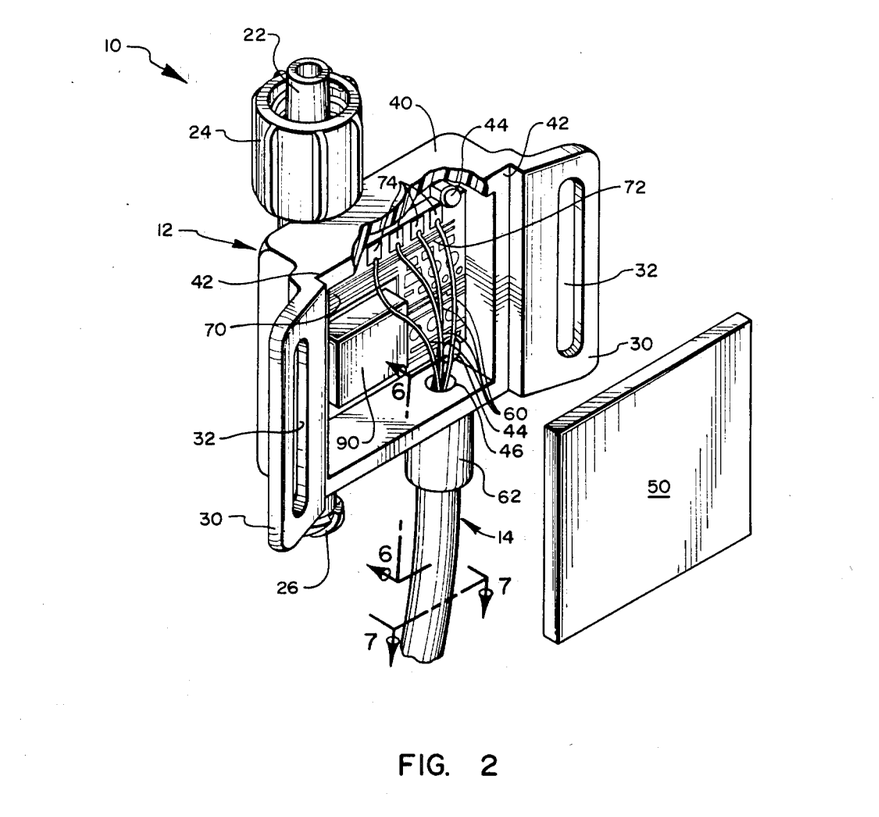
FIG. 2 is a partially exploded perspective view illustrating one presently preferred embodiment of the disposable pressure transducer apparatus of the present invention.

One presently preferred configuration for housing 12 of transducer apparatus 10 is illustrated in FIGS. 1 and 2. As shown, coupling tube 20 of housing 12 is provided with suitable connectors for connecting coupling tube 20 to an indwelling, fluid-filled catheter (not shown). These connectors may comprise virtually any suitable connectors, such as standard luer lock connectors. Thus, for example, coupling tube 20 is illustrated herein as having a luer lock nut 24 attached to one end 22 thereof, while the other end 26 of coupling tube 20 is configured as a threaded female luer lock connector.

Housing 12 may advantageously comprise some means for mounting transducer apparatus 10 to the arm of a patient or to another structure. Thus, as illustrated herein, housing 12 may comprise a pair of mounting brackets 30 which are either secured to or formed integrally with housing 12. As shown, mounting brackets 30 may also have slots 32 formed therein through which tape or straps may be positioned to secure the housing. Thus, using mounting brackets 30, together with a suitable strap or fasteners (not shown), transducer apparatus 10 can be mounted to an I.V. poll, to a fluid manifold adjacent the patient's bedside, or to the patient himself.

Housing 12 may be configured in any suitable manner. For example, as shown best in FIG. 2, housing 12 may comprise a shell 40 and a back plate 50. Further, as illustrated, shell 40 may be provided with a recessed shelf 42, and back plate 50 may be formed so as to fit snugly within recessed shelf 42. Back plate 50 may then be secured to shell 40 in some suitable manner, such as, for example, by means of an adhesive or by sonic welding.

It will be readily appreciated that housing 12 of transducer apparatus 10 could also have a wide variety of different shapes. Thus, although housing 12 is illustrated herein as being a substantially cubical structure, it will be appreciated that housing 12 could also be formed as a substantially cylindrical or ellipsoid structure. Additionally, housing 12 could be formed as part of another intravenous device. For example, housing 12 could be formed as part of an intravenous continuous flush device.

Also, housing 12 may have any suitable dimensions. Preferably, however, housing 12 is relatively small so as to both reduce manufacturing costs and allow a patient substantial freedom of movement when transducer apparatus 10 is attached directly to such patient. Thus, for example, one presently preferred embodiment of housing 12 is approximately one inch (2.54 cm) wide, 1.5 inches (3.81 cm) long, and 0.5 inch (1.27 cm) deep.

Further, housing 12 may be formed of a wide variety of substances. For example, housing 12 may be formed of a suitable plastic material by conventional injection molding techniques. Advantageously, in order to facilitate removing any air bubbles which might collect in coupling tube 20 of housing 12, housing 12 may be formed so as to be at least partially transparent.

As illustrated in FIG. 2, the various electrical components of transducer apparatus 10 are secured within housing 12. As shown, such electrical components are mounted on a dielectric substrate sheet 70. Substrate 70 may be formed of any of a number of suitable dielectric materials, such as, for example, a ceramic material. Substrate 70 is, in turn, secured within housing 12. For example, housing 12 may be provided with suitable stakes 44 which may be flattened by means of sonic welding techniques over a portion of substrate 70 after substrate 70 is appropriately positioned within housing 12 between the stakes 44 (see also FIG. 3).

As schematically shown in FIG. 2, substrate 70 is provided with a conventional temperature compensation circuit 72. Temperature compensation circuit 72 is used to adjust both the zero pressure point and the gain of transducer apparatus 10 such that these parameters will not change with variations in temperature. Temperature compensation circuit 72 also determines the gain or sensitivity of transducer apparatus 10, such gain being typically on the order of approximately five microvolts per volt of excitation per millimeter of mercury pressure. Further, temperature compensation circuit 72 is used to match the input and output impedance of transducer apparatus 10 with that of the monitor device (not shown), typical impedances being about 350 ohms.

Temperature compensation circuit 72 may be provided on substrate 70 in any suitable manner. For example, temperature compensation circuit 72 may be provided using appropriate silk-screening techniques. Thereafter, the various components of temperature compensation circuit 72 may be laser-trimmed to the required values by means which are known in the art. As further depicted in FIG. 2, substrate 70 is also provided with solder pads 74. Solder pads 74 are electrically connected to temperature compensation circuit 72, and solder pads 74, thus, provide a means for electrically connected circuit 72 to cable 14.

Cable 14 is connected to housing 12 in some suitable manner, such as, for example, by means of a connecting sheath 62. Conductors 60 of cable 14 then enter housing 12 through a hole 46, and conductors 60 are thereafter appropriately connected to solder pads 74.

Significantly, in order to obtain accurate pressure measurements, the pressure readings of transducer apparatus 10 should be referenced to some substantially constant pressure. This may easily be done by referencing the pressure readings to atmospheric pressure. To this end, as discussed further below, the interior of housing 12 is continuously vented to atmospheric pressure by means of a vent channel in cable 14. Such vent channel communicates both with the interior of housing 12 through hole 46 and with the atmosphere through a suitable vent port located somewhere along cable 14, such as, for example, in a connector of cable 14. Thus, by providing an open air passageway to and from housing 12, the vent channel of cable 14 assures that the interior of housing 12 is continuously maintained at atmospheric pressure.

Cable 14 may comprise virtually any suitable cable having multiple conductors. In addition, cable 14 should be shielded so as to minimize electromagnetic interference with the signals being transmitted along cable 14. Thus, for example, cable 14 may comprise four individually insulated conductors which are surrounded by a woven conductive shield, all of which are surrounded by a suitable insulating material. A vent channel through cable 14 may then be provided by simply removing one of the conductors so as to provide some space within cable 14.

It should be noted, however, that if the cable 14 of transducer apparatus 10 is formed in the manner just described, cable 14 will be relatively expensive (typically on the order of 70¢ to $1.00 per foot). As a result, a long length of cable 14 cannot be economically incorporated as part of a disposable unit. In such case, cable 14 could be formed as a short (e.g., one foot) length of cable having a connector on the end thereof. A reusable, longer cable may then be used to connect cable 14 and transducer apparatus 10 to a monitor device.

There are, however, some significant disadvantages to using a short cable 14 with such a longer connecting cable. First, the longer cable (which is reusable), is contaminated due to its being repeatedly run over by medical equipment and stepped on by medical personnel and others. Consequently, the use of such a cable may give rise to concerns regarding adequate asepsis. In addition, a longer connecting cable can be quite inconvenient to use, in that it is first necessary to locate and then untangle a suitable cable and thereafter properly connect it to both cable 14 and a monitor. Significantly, in an operating room, where there are typically many cables being used, such a procedure can be quite confusing.

Figure 6:
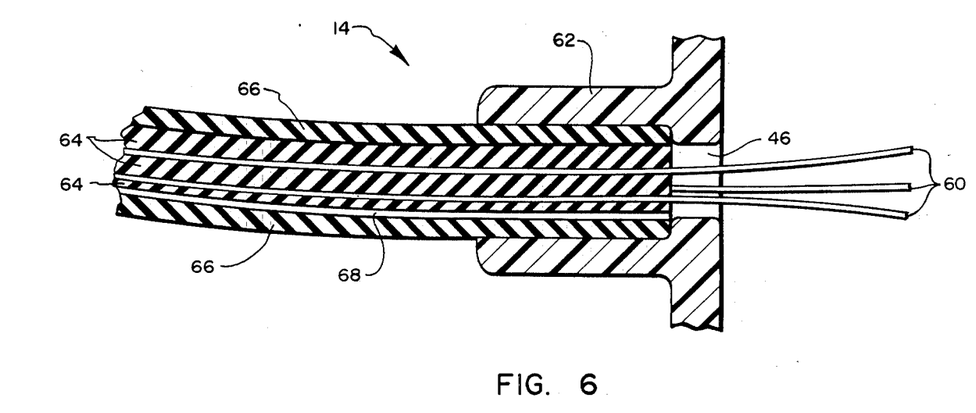
FIG. 6 is an enlarged, cross-sectional view taken along lines 6—6 of FIG. 2 and illustrating one presently preferred embodiment of a cable for connecting the disposable pressure transducer apparatus of the present invention to a monitor device.
Figure 7:
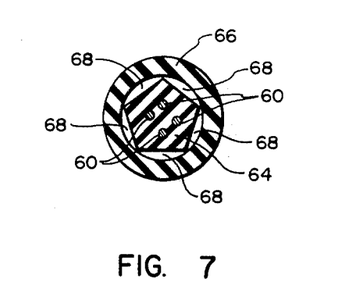
FIG. 7 is an enlarged, cross-sectional view taken along lines 7—7 of FIG. 2.

The above-mentioned disadvantage can be overcome by forming cable 14 in the manner illustrated in FIGS. 6 and 7. As shown, cable 14 may be formed so as to comprise a plurality of magnet wire conductors 60. Since magnet wires are typically already insulated, they do not require a separate insulation coating. As a result, the cost of providing such a coating is eliminated. The magnet wires 60 may then be surrounded by a conductive polyvinyl chloride shield 64, which is much less expensive than a woven shield; and the polyvinyl chloride shield may be surrounded with a suitable insulator material 66. Advantageously, this type of construction for cable 14 significantly reduces the cost of cable 14 such that a longer length of cable 14 can be made disposable.

When cable 14 is formed in the above-described manner, the vent channel of cable 14 may be readily provided by forming the polyvinyl chloride shield 64 and the insulator material 66 such that a space 68 is provided between insulator 66 and polyvinyl chloride shield 64 along at least a portion of cable 14. It will be readily appreciated that polyvinyl chloride shield 64 and insulator material 66 may be configured in a wide variety of ways so as to form such a space 68. For example, as depicted in FIG. 7, polyvinyl chloride shield 64 may be configured so as to be substantially polygonal in cross-section, while insulator material 66 is substantially cylindrical. Alternatively, polyvinyl chloride shield 64 could be formed with suitable spacing members so as to provide a space 68, or polyvinyl chloride shield 64 could be formed as a substantially cylindrical member whose outside diameter is somewhat less than the inside diameter of insulator 66.

As further depicted in FIG. 2, an opaque cap 90 is also secured to substrate 70. As described below, cap 90 houses the semiconductor pressure transducer and the associated electrical connections between the pressure transducer and the compensation circuit 72.

Figure 3:
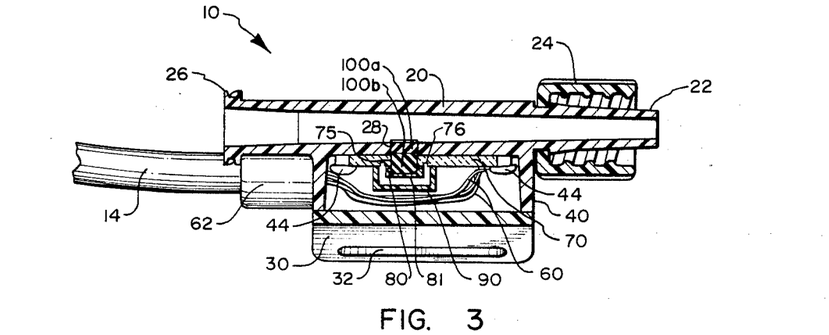
FIG. 3 is a cross-sectional view taken along lines 3—3 of FIG. 1.
Figure 4:
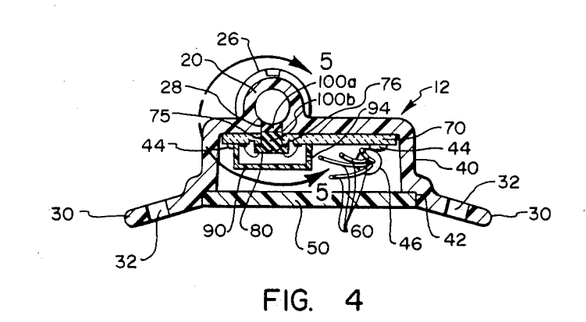
FIG. 4 is a cross-sectional view taken along lines 4—4 of FIG. 1.
Figure 5:
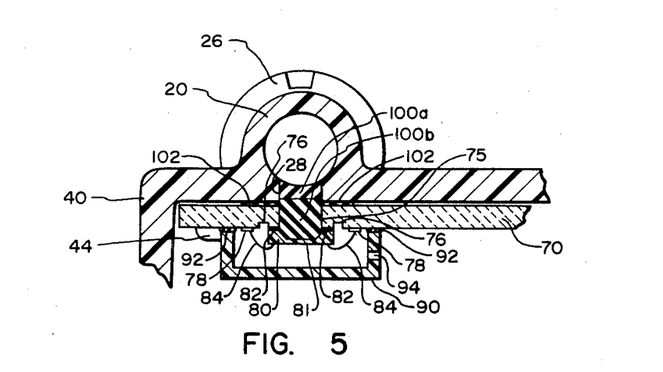
FIG. 5 is an enlarged, cross-sectional view taken along lines 5—5 of FIG. 4.

The attachment of the semiconductor pressure transducer 80 of transducer apparatus 10 is depicted in FIGS. 3 through 5. Pressure transducer 80 is formed by methods which are well-known in the art so as to include the required piezoresistive pressure diaphragm and measuring circuitry. For example, four resistive elements are ion-implanted on pressure transducer 80 so as to form a conventional Wheatstone bridge. In addition, a central portion of pressure transducer 80 is etched away (such as, for example, by chemical etching techniques), so as to form a piezoresistive diaphragm 81. If, for example, pressure transducer 80 is 0.020 inches (0.508 mm) thick, diaphragm 81 could be formed so as to be approximately 0.0015 inches (0.0381 mm) thick.

As illustrated in FIGS. 3 through 5, substrate 70 has a hole 75 therethrough. In addition, housing 12 has a passageway 28 formed therein which extends from the passageway of coupling tube 20 to the interior of housing 12. As shown, substrate 70 is mounted within housing 12 such that passageway 28 communicates with hole 75 in substrate 70. Pressure transducer 80 is then mounted directly to substrate 70 such that piezoresistive diaphragm 81 of pressure transducer 80 is positioned directly over hole 75 in substrate 70.

Importantly, pressure transducer 80 is mounted to substrate 70 such that thermal expansion and contraction of pressure transducer 80 will not subject pressure transducer 80 to mechanical stress which might cause incorrect, transient pressure readings. Thus, for example, pressure transducer 80 is secured with an adhesive material which is flexible enough to permit pressure transducer 80 to thermally expand and contract without significant interference. Such an adhesive may, for example, comprise a suitable silicone adhesive. It should be noted that mounting pressure transducer 80 directly to substrate 70 in this manner, thereby eliminating the need for a separate pyrex pedestal, reduces the time and cost required for manufacture and assembly.

As shown best in FIG. 5, a channel 76 is formed around hole 75 in substrate 70 such that channel 76 surrounds pressure transducer 80 when pressure transducer 80 is properly mounted over hole 75 on substrate 70. If, for example, substrate 70 is approximately 0.040 inches (1.016 mm) thick, channel 76 may be within the range of approximately 0.010 inches (0.254 mm) to 0.020 inches (0.508 mm) deep. Channel 76 helps further isolate pressure transducer 80 from mechanical stress. For example, upon a flexing or bending of substrate 70 and/or housing 12, channel 76 helps to mechanically isolate pressure transducer 80 from the bending movement and, thus, helps minimize the occurrence of any inaccurate, resulting, transient signals.

As also depicted in FIG. 5, diaphragm 81 of pressure transducer 80 is electrically connected to the circuitry on substrate 70 in some suitable manner. For example, as shown, solder pads 78 are provided on substrate 70, and wires 84 are connected between pressure transducer 80 and solder pads 78.

As mentioned above, a cap 90 is secured to substrate 70 so as to cover pressure transducer 80. Cap 90 thus protects pressure transducer 80, together with the associated wires 84 and solder pads 78, from mechanical injury. In addition, cap 90 is formed of an opaque material so as to prevent light from penetrating cap 90. Therefore, cap 90 also shields pressure transducer 80 from exposure to light and prevents transient signals from being generated by pressure transducer 80 as the transducer apparatus 10 is exposed to various light sources. As shown best in FIG. 5, cap 90 is secured to substrate 70 by means of a suitble adhesive 92. Adhesive 92 may, for example, comprise an epoxy resin adhesive.

As shown best in FIG. 5, cap 90 is provided with a vent hole 94 such that pressure transducer 80 is vented to the interior of housing 12. Since housing 12 is vented to atmospheric pressure, as described above, pressure transducer 80 is also vented to atmospheric pressure. Thus, the pressure measured by pressure transducer 80 will be referenced to atmospheric pressure at all times, as is desirable.

In order to provide additional shielding from light, one side of substrate 70 may be coated, at least in part, by some type of opaque coating. Such an opaque coating may, for example, comprise an opaque glass which is coated onto one side of substrate 70 so as to surround pressure transducer 80. It will be appreciated that such opaque coating reduces the likelihood that light will penetrate substrate 70 and contact pressure transducer 80. Thus, such coating helps further eliminate transient fluctuations in the output signal as transducer apparatus 10 is exposed to various light sources.

Passageway 28 of housing 12 and hole 75 in substrate 70 are filled with a suitable gel 100a and 100b (generally referred to as gel 100), which provides a hydraulic coupling for transmission of pressure pulses from the passageway of coupling tube 20 to pressure transducer 80. For example, gel 100 may comprise a silicone gel. In addition, a portion 100b of gel 100 may be opaque so as to further prevent light from contacting pressure transducer 80 and causing inaccurate readings.

As further depicted in FIG. 5, a portion of gel 100 extends into the space between housing 12 and substrate 70 so as to effectively form a fluid-tight seal 102 which seals housing 12 and substrate 70 and electrically isolates substrate 70 and its associated circuitry from the saline solution carried by tube 20. This increases the safety of the device by helping to prevent electrical shock hazard to the patient. Advantageously, fluid-tight seal 102 may also be opaque so as to assist in shielding transistor chip 80 from light.

Significantly, the above-described structure of transducer apparatus 10 greatly facilitates the manufacture of the apparatus. First, substrate 70 is formed and provided with a suitable hole 75. Substrate 70 may then be provided with an opaque coating, and a temperature compensation circuit 72 is thereafter silk-screened onto substrate 70. Advantageously, several substrate sections may be formed simultaneously as part of a large sheet of substrate material, each substrate portion 70 being provided with an appropriate hole 75. In such case, an opaque coating may then be provided on one side of the entire substrate sheet; and a temperature compensation circuit 72 may be provided on substrate portion 70 a batch at a time by simultaneously silk screening a temperature compensation circuit 72 onto each substrate portion 70 of the large substrate sheet.

Pressure transducer 80 is next mounted on substrate 70 with a suitable adhesive 82. Wires 84 are thereafter connected to solder pads 78 and to pressure transducer 80, and cap 90 is secured to substrate 70 by means of adhesive 92. The circuitry is then tested (i.e., pressure and temperature cycled), and temperature compensation circuit 72 is laser-trimmed, as required.

Once the above-described components are assembled onto substrate 70, an opaque gel 100b may be placed in hole 75 of substrate 70. Substrate 70 may then be secured within upper shell 40 of housing 12 by means of stakes 44. A clear gel 100a may thereafter be placed in passageway 28 of housing 12. During this process, a portion of gel 100 will have run into the space between substrate 70 and shell 40, so as to form a fluid-tight seal 102. Gel 100 may then be oven-cured to the appropriate consistency using conventional oven-curing techniques.

Thereafter, cable 14 may be attached to shell 40 of housing 12, and conductors 60 of cable 14 may be connected to the appropriate solder pads 74. Finally, plate 50 may be secured to shell 40, and transducer apparatus 10 is then ready to be packaged and sterilized for use. Importantly, because of the foregoing procedure, the need to perform a large number of separate delicate assembly steps is eliminated, thereby helping to reduce the overall cost of the apparatus.

To use transducer apparatus 10, coupling tube 20 is first connected to the fluid-filled catheter extending from the patient. Optionally, coupling tube 20 may be connected so as to be directly in-line with a continuous flush device, such that fluid flows through the coupling tube 20 and toward the patient. Alternatively, coupling tube 20 may be connected so as to be outside of the direct fluid flow path, with one end 22 or 26 of coupling tube 20 being blocked as with a stopcock. Coupling tube 20 is then filled with fluid, and any air bubbles are removed. As pressure pulses are thereafter transmitted along the fluid column of the catheter, such pressure pulses enter the passageway of coupling tube 20 and are transmitted through gel 100 to pressure transducer 80. Pressure transducer 80 measures such pressure pulses, and electrical signals representing such pressure pulses are transmitted along cable 14 to a monitor. When a patient no longer requires blood pressure monitoring, transducer apparatus 10 may be disconnected and discarded.

From the above discussion, it will be appreciated that the present invention provides an accurate, safe and inexpensive, disposable pressure transducer apparatus for monitoring human blood pressure. Since all of the pressure sensing components, including the semiconductor pressure transducer, are secured to the same side of a dielectric substrate sheet, the present invention provides a disposable pressure transducer apparatus which has a minimum number of component parts such that the transducer apparatus is easy to manufacture and assemble. Additionally, due to the use of an opaque covering cap, an opaque coating, and an opaque silicone gel, the present invention further provides a disposable pressure transducer apparatus wherein the semiconductor pressure transducer of the apparatus is effectively shielded from exposure to light. Further, since all of the electrical components of the apparatus are mounted on the side of the dielectric substrate which is away from the fluid channel, and since a fluid-tight silicone gel seal is formed between the other side of the dielectric substrate and the housing, the present invention provides a disposable pressure transducer apparatus wherein the electrical circuitry of the apparatus is electrically isolated from the patient, thereby minimizing the likelihood that the patient will receive an electrical shock.

The invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by U.S. Letters Patent is:

1. In a direct blood pressure measurement system having a monitor device coupled to an indwelling, fluid-filling catheter adapted to be inserted into a patient, a disposable pressure transducer apparatus with a dielectric substrate having first and second sides and a pressure transducer having a piezoresistive pressure diaphragm secured to said first side of said substrate, said apparatus comprising:

means circuit for temperature compensation provided on said first side of said substrate, said circuit means being electrically connected to said pressure diaphragm;

means for electrically connecting said circuit means for temperature compensation and said pressure transducer to said monitor device, said connecting means being attached to said circuit means and said pressure transducer on said first side of the substrate;

means for housing said substrate, said housing means comprising a first passageway communicating with said fluid-filled catheter, a second passageway providing fluid communication between said pressure diaphragm and said first passageway, and means for mounting said substrate in said housing means such that said second side of the substrate faces toward said second passageway and said first side of the substrate faces away from said second passageway; and means for hydraulically coupling said pressure diaphragm through said second passageway to said first passageway and the fluid-filled catheter communicating with said first passageway.

2. An system as defined in claim 1 further comprising means for forming a fluid-tight seal between said second side of said substrate and the portion of said housing means through which said second passageway is formed.

3. A system as defined in claim 2 wherein said means for forming said fluid-tight seal comprises a silicone gel interposed between said second side of said substrate and a portion of said housing means adjacent said second passageway formed through said housing means.

4. A system as defined in claim 1 further comprising means for shielding said pressure transducer from exposure to light.

5. A system as defined in claim 4 wherein said means for shielding said pressure transducer from exposure to light comprises an opaque coating formed on at least one of said first and second sides of said substrate.

6. A system as defined in claim 4 wherein said means for shielding said pressure transducer from exposure to light comprises an opaque cap secured to said dielectric substrate so as to cover said pressure transducer, said opaque cap also protecting said pressure transducer from mechanical injury.

7. A system as defined in claim 1 wherein said means for electrically connecting said circuit-means for temperature compensation and said pressure transducer to said monitor device comprises:

a plurality of solder pads secured on said first side of said substrate, said solder pads being electrically connected to said temperature compensation and said pressure transducer; and a plurality of electrical conductors, at least one of said electrical conductors being connected to each said solder pad.

8. A system as defined in claim 7 wherein said electrical conductors comprise insulated magnet wires having a conductive polyvinyl chloride shield surrounding said magnet wires, and an insulator material surrounding said conductive polyvinyl chloride shield.

9. A system as defined in claim 1 wherein said means for electrically connecting said circuit means for temperature compensation and said pressure transducer to said monitor device comprises means for venting a first side of said pressure diaphragm to atmospheric pressure.

10. A system as defined in claim 9 wherein said means for electrically connecting said circuit means for temperature compensation and said pressure transducer to said monitor device comprises a cable having a plurality of electrical conductors therethrough which are connected to said circuit means for temperature compensation and said pressure transducer, and wherein said means for venting said first side of said pressure diaphragm comprises a space formed through the interior of said cable.

11. A system as defined in claim 1 wherein said means for hydraulically coupling said pressure diaphragm through said second passageway comprises a hole formed in said substrate under said diaphragm, and a silicone gel which substantially fills said second passageway and said hole so as to be in contact with said diaphragm.

12. A system as defined in claim 11 wherein at least a portion of said gel is comprised of a material which is substantially clear so as to be essentially indistinguishable in relation to said housing means through which said second passageway is formed.

13. A system as defined in claim 11 wherein at least a portion of said gel is comprised of a material which is substantially opaque, thereby shielding one side of said pressure transducer from exposure to light.

14. In a direct blood pressure monitoring system having a monitor device coupled to an indwelling, fluid-filled catheter adapted to be inserted into a patient, a disposable pressure transducer apparatus with a dielectric substrate having first and second sides and a pressure transducer having a piezoresistive pressure diaphragm secured to said first side of said substrate, said apparatus comprising:

circuit means for temperature compensation provide on said first side of said substrate, said means circuit being electrically connected to said pressure diaphragm;

means for a housing said substrate, said housing means comprising a first passageway communicating with said fluid-filled catheter, a second passageway providing fluid communication between said pressure diaphragm and said first passageway, and means for mounting said substrate in said housing means such that said second side of the substrate faces toward said second passageway and said first side of the substrate faces away from said second passageway;

an electrical cable comprising a plurality of separate electrical conductors, said cable being connected to said housing means and said conductors being attached to said circuit means for temperature compensation and said pressure transducer on said first side of said substrate;

means for hydraulically coupling said pressure diaphragm through said second passageway to said first passsageway; and means for forming a fluid-tight seal between said second side of said substrate and the portion of said housing means comprising said second passageway, such that said first side of said substrate together with said pressure transducer and the circuit means for temperature compensation mounted thereon are electrically isolated from said fluid-filled catheter adapted to be inserted into said patient.

15. A system as defined in claim 14 further comprising means for shielding said pressure transducer from exposure to light.

16. A system as defined in claim 15 wherein said means for shielding said pressure transducer from exposure to light comprises an opaque coating formed on at least one of said first and second sides of said substrate.

17. A system as defined in claim 15 wherein said means for shielding said pressure transducer from exposure to light comprises an opaque cup secured to said dielectric substrate so as to cover said pressure transducer, said opaque cap also protecting said pressure transducer from mechanical injury.

18. A system as defined in claim 17 wherein said cap has a hole formed therethrough and wherein said cable has a space formed through the interior of said cable, said hole formed in said cap and the space formed through said cable together providing a means for venting one side of said pressure diaphragm to atmospheric pressure while the other side of said pressure diaphragm is in fluid communication with said fluid-filled catheter.

19. A system as defined in claim 14 wherein said electrical conductors comprise insulated magnet wires having a conductive polyvinyl chloride shield surrounding said magnet wires, and an insulator material surrounding said conductive polyvinyl chloride shield.

20. A system as defined in claim 14 further comprising means for venting one side of said pressure diaphragm to atmospheric pressure while the other side of said diaphragm is in fluid communication with said fluid-filled catheter.

21. A system as defined in claim 14 wherein said means for hydraulically coupled said pressure diaphragm and wherein said means for forming said fluid-tight seal comprise a silicone gel, said gel filling substantially the entire second passageway of said housing means and said gel also being interposed between said substrate and a portion of said housing means through which said second passageway is formed.

22. A system as defined in claim 21 wherein said substrate has a hole formed therethrough and positioned under said pressure diaphragm, and wherein said gel fills the hole formed through said substrate so as to be in contact with one side of said pressure diaphragm.

23. A system as defined in claim 21 wherein at least a portion of said gel is comprised of a material which is substantially clear so as to be essentially indistinguishable in relation to said portion of the housing means through which said second passageway is formed.

24. A system as defined in claim 23 wherein a portion of said gel is comprised of a material which is substantially opaque, thereby shielding one side of said pressure transducer from exposure to light.

25. In a direct blood pressure monitoring system having a monitor device coupled to an indwelling, fluid-fille catheter adapted to be inserted into a patient, a disposable pressure transducer apparatus with a dielectric substate having first and second sides and a pressure transducer having a piezoresistive pressure diaphragm secured to said first side of said substrate, said apparatus comprising:

circuit means for temperature compensation provided on said first side of said substrate, said circuit means being electrically connected to said pressure diaphragm;

means for housing said substrate, said housing means comprising a first passageway communicating with said fluid-filled catheter, a second passageway providing fluid communication between said pressure diaphragm and said first passageway, and means for mounting said substrate in said housing means such that said second side of the substrate faces toward said second passageway and said first side of the substrate faces away from said second passageway;

means for shielding said pressure transducer from exposure to light, said shielding means comprising an opaque coating formed on at least one of said first and second sides of said substrate and an opaque cap secured to the first side of said substrate so as to cover said pressure transducer, said cap having a hole formed therethrough;

an electrical cable comprising a plurality of separate electrical conductors, said cable being connected to said housing means and said conductors being attached to said circuit means for temperature compensation and said pressure transducer on said first side of the substrate, and said cable having a space formed through the interior of said cable, the space through said cable and the hole formed through said cap together providing a means for venting one side of the pressure transducer to atmospheric pressure; and a gel substance which substantially fills said second passageway formed through said housing means, said gel substance being in contact with the other side of said pressure diaphragm and said gel substance also being interposed between said substrate and a portion of said housing means adjacent said second passageway so as to form a fluid-tight seal between said substrate and said housing means.

* * * * *